United States Patent
Takahara

(10) Patent No.: US 10,379,066 B2
(45) Date of Patent: Aug. 13, 2019

(54) X-RAY TRANSMISSION INSPECTION APPARATUS

(71) Applicant: Hitachi High-Tech Science Corporation, Tokyo (JP)

(72) Inventor: Toshiyuki Takahara, Tokyo (JP)

(73) Assignee: Hitachi High-Tech Science Corporation, Tokyo (JP)

( * ) Notice: Subject to any disclaimer, the term of this patent is extended or adjusted under 35 U.S.C. 154(b) by 218 days.

(21) Appl. No.: 15/685,612

(22) Filed: Aug. 24, 2017

(65) Prior Publication Data

US 2018/0059035 A1 Mar. 1, 2018

(30) Foreign Application Priority Data

Aug. 24, 2016 (JP) .................................. 2016-163437

(51) Int. Cl.
*G01N 23/04* (2018.01)
*G01N 23/10* (2018.01)

(52) U.S. Cl.
CPC ............. *G01N 23/04* (2013.01); *G01N 23/10* (2013.01)

(58) Field of Classification Search
CPC ................................ G01N 23/04; G01N 23/10
See application file for complete search history.

(56) References Cited

U.S. PATENT DOCUMENTS

| 2004/0096029 | A1* | 5/2004 | Shiota | ...................... A61B 6/04 378/42 |
| 2010/0046700 | A1* | 2/2010 | Sakai | .................... G01N 23/223 378/44 |
| 2015/0276626 | A1* | 10/2015 | Matoba | ................ G01N 23/083 378/69 |
| 2015/0359504 | A1* | 12/2015 | Zhou | ...................... A61B 6/547 378/38 |
| 2015/0362445 | A1* | 12/2015 | Takahashi | ........ G01N 35/00693 378/44 |
| 2017/0018467 | A1* | 1/2017 | Walker | ................... G01N 23/04 |

FOREIGN PATENT DOCUMENTS

JP 2004-257884 A 9/2004

* cited by examiner

*Primary Examiner* — Marcus H Taningco
(74) *Attorney, Agent, or Firm* — Stinson LLP

(57) ABSTRACT

An X-ray transmission inspection apparatus capable of easily performing the adjustment by a standard sample is provided. The apparatus is provided with an X-ray source; an X-ray detector; a standard sample moving mechanism configured to move a standard sample placed in a different position from that of a sample; and an arrangement changing mechanism configured to be in a such a manner that the X-ray source and the X-ray detector, and the sample and the standard sample are movable relative to each other, and configured to change an arrangement state from one arrangement state in which the X-ray source and the X-ray detector face the sample to the other arrangement state in which the X-ray source and the X-ray detector face the standard sample that is moved by the standard sample moving mechanism.

6 Claims, 8 Drawing Sheets

X-RAY TRANSMISSION INSPECTION APPARATUS

CROSS-REFERENCE TO RELATED APPLICATION

The present application claims priority to Japanese Patent Application No. 2016-163437, filed Aug. 24, 2016, the entire contents of which is incorporated herein for all purposes by this reference.

BACKGROUND

The present invention relates to an X-ray transmission inspection apparatus which is capable of detecting minute foreign matters and the like in a sample and which can easily perform adjustment such as calibration of inspection.

Generally, in order to detect foreign matters such as minute metals or the like in a sample, an X-ray transmission inspection is used in which an X-ray transmission image acquired by irradiating X-rays to the sample is inspected. For example, in recent years, in lithium-ion secondary batteries adopted in automobiles, hybrid vehicles, electric vehicles, and the like, an electrode, as an anode, is formed in such a manner that a lithium manganese oxide film or a lithium cobalt oxide film is formed on both surfaces of an Al film. Therefore, if foreign matters, such as Fe (iron), SUS (stainless) or the like, of several tens of micrometers or lager are mixed into the battery, a short circuit may occur, thereby causing burning of the battery or degradation of performance. Therefore, mixed foreign matters are detected by X-ray transmission inspection and removed during production.

In an X-ray transmission inspection apparatus for detecting foreign matters or the like in a sample, it is well known that, when conducting an in-line inspection, an X-ray source and an X-ray detector such as a line sensor are arranged to face each other with a sample moving in one direction placed therebetween. For example, a convention solution proposes an X-ray foreign matter inspection apparatus that detects even a minute foreign matter with high sensitivity by using a time delay integration sensor (TDI sensor). In this X-ray foreign matter inspection apparatus, foreign matters are detected by synchronizing the moving speed of the sample with the charge transfer speed of the TDI sensor.

The above-described conventional technique poses the following problems. That is, in the conventional X-ray transmission inspection apparatus, when it is desired to perform adjustment (calibration or the like) of the X-ray source and the X-ray detector by using a standard sample whose size and position are previously known, since the X-ray source and the X-ray detector have been arranged so as to face a moving sample, it was necessary to inspect the standard sample by placing the standard sample placed at the same position as the sample instead of the sample. In addition, after the inspection of the standard sample, it was also necessary to reposition the sample to its original position. For this reason, an operation of replacing the sample with the standard sample is necessary, which causes a problem that the inspection operation must be interrupted for a long time. Particularly, when a belt-shaped sample is inspected, since the inspection is performed while the sample flows continuously by a roll-to-roll method, it is difficult to perform the inspection by interrupting the inspection and replacing the sample with the standard sample.

SUMMARY

The present invention has been made in view of the above-described problems, and it is an object of the present invention to provide an X-ray transmission inspection apparatus capable of easily performing the adjustment by a standard sample.

Embodiments of the present invention adopt the following configuration in order to solve the above problem. That is, according to an X-ray transmission inspection apparatus of a first aspect of this invention, there is provided an X-ray transmission inspection apparatus comprising, an X-ray source that irradiates X-rays to a sample; a sample moving mechanism that moves the sample continuously in a predetermined direction while X-rays are irradiated from the X-ray source; an X-ray detector that is provided opposed to the X-ray source with respect to the sample and detects the X-rays transmitted through the sample; a standard sample moving mechanism configured to move a standard sample placed in a different position from that of the sample; and an arrangement changing mechanism configured to be in a such a manner that the X-ray source and the X-ray detector, and the sample and the standard sample are movable relative to each other, and configured to change an arrangement state from one arrangement state in which the X-ray source and the X-ray detector face the sample to the other arrangement state in which the X-ray source and the X-ray detector face the standard sample that is moved by the standard sample moving mechanism.

In this X-ray transmission inspection apparatus, there is provided the arrangement changing mechanism configured to be in a such a manner that the X-ray source and the X-ray detector, and the sample and the standard sample are movable relative to each other, and configured to change an arrangement state from one arrangement state in which the X-ray source and the X-ray detector face the sample to the other arrangement state in which the X-ray source and the X-ray detector face the standard sample that is moved by the standard sample moving mechanism. Accordingly, when performing adjustment such as calibration by the standard sample, since the X-ray source and the X-ray detector can be retracted by the arrangement changing mechanism from the line which is the inspection position of the sample and then the inspection of the standard sample can be performed, there is no interference with the sample, and maintenance of the inspection unit, etc. becomes easy. Therefore, since the operation for replacing the sample with the standard sample is not required, it is unnecessary to remove the sample from the inspection line even during inspection of a plurality of samples or a long sample, and then the adjustment such as calibration or the like can be easily performed.

The X-ray transmission inspection apparatus of a second aspect of the present invention according to the first aspect of this invention is characterized in that a plurality of inspection units each comprising the X-ray source and the X-ray detector opposed to each other are provided, and that the arrangement changing mechanism is configured to move the plurality of inspection units.

That is, in this X-ray transmission inspection apparatus, since the arrangement changing mechanism can move a plurality of inspection units, it is possible to adjust the plurality of inspection units simultaneously or individually by the standard sample.

The X-ray transmission inspection apparatus of a third aspect of the present invention according to the first or second aspect of this invention is characterized in that the sample is a belt-shaped sample, and the sample moving mechanism moves the sample in its extending direction, and that the standard sample moving mechanism is configured to move the standard sample arranged on the side of the sample at the same speed as the sample in a direction parallel to the moving direction of the sample.

That is, in this X-ray transmission inspection apparatus, since the standard sample moving mechanism can move the standard sample arranged on the side of the sample at the same speed as the sample in the direction parallel to the moving direction of the sample, it is possible to easily inspect the standard sample under the same conditions as the sample by merely moving the X-ray source and the X-ray detector, by the arrangement changing mechanism, to the opposite positions facing the standard sample on the side of the belt-like sample.

The X-ray transmission inspection apparatus of a fourth aspect of the present invention according to any one of the first aspect to third aspect of this invention, further comprises a control unit which is connected to the X-ray source and the X-ray detector to control the X-ray source and the X-ray detector, wherein the control unit is configured to perform the adjustment of the X-ray source and the X-ray detector when inspecting the sample based on the result of inspecting the standard sample.

That is, in this X-ray transmission inspection apparatus, since the control unit adjusts the X-ray source and the X-ray detector when inspecting the sample based on the result of inspecting the standard sample, the control unit automatically performs the adjustment such as the calibration or the like of the X-ray source and the X-ray detector, and then it is possible to maintain stable and highly accurate measurement.

The X-ray transmission inspection apparatus of a fifth aspect of the present invention according to the second aspect of this invention is characterized in that the arrangement changing mechanism is configured to move the plurality of the inspection units to different positions in the width direction of the sample when inspecting the sample.

That is, in this X-ray transmission inspection apparatus, since the arrangement change mechanism can move the plurality of inspection units to different positions in the width direction of the sample when inspecting the sample, the width direction of the sample is divided into a plurality of positions, and it is possible to inspect different positions in the width direction of the sample separately by the inspection units. Therefore, even if it is not a large-sized inspection unit, it is possible to perform inspection in a wide range in the width direction of the sample with a plurality of small inspection units, and it is also possible to perform inspection by irradiating X-rays only to specific positions in the width direction. In addition, by moving the plurality of inspection units to positions facing the standard sample, it is possible to inspect the plurality of inspection units simultaneously or individually with the standard sample.

The X-ray transmission inspection apparatus of a sixth aspect of the present invention according to the second aspect of this invention is characterized in that the arrangement changing mechanism is configured to move the plurality of the inspection units in the same position in the width direction of the sample when inspecting the sample.

That is, in this X-ray transmission inspection apparatus, since the arrangement changing mechanism is capable of moving the plurality of inspection units to the same position in the width direction of the sample when inspecting the sample, it is possible to inspect the same position of the sample by the plurality of inspection units in a multistage manner and then foreign matters can be detected with higher accuracy. Further, by changing the type of ray of the respective X-ray source to specialize on sensitivities to a plurality of different foreign matters such as Fe and Pt, it is possible to detect the plurality of different foreign matters by a single inspection. Furthermore, it is also possible to increase the scanning speed of the sample by inspecting the same position with the plurality of inspection units According to aspects of the present invention, the following effects are achieved.

That is, according to the X-ray transmission inspection apparatus of the present invention, there is provided the arrangement changing mechanism configured to be in a such a manner that the X-ray source and the X-ray detector, and the sample and the standard sample are movable relative to each other, and configured to change an arrangement state from one arrangement state in which the X-ray source and the X-ray detector face the sample to the other arrangement state in which the X-ray source and the X-ray detector face the standard sample that is moved by the standard sample moving mechanism. Therefore, since the operation for replacing the sample with the standard sample is not required, it is unnecessary to remove the sample from the inspection line even during inspection of a plurality of samples or a long sample, and then the adjustment such as calibration or the like can be easily performed.

Other objects and features will be in part apparent and in part pointed out hereinafter.

BRIEF DESCRIPTION OF THE DRAWINGS

The above and other objects, features and other advantages of the present invention will be more clearly understood from the following detailed description when taken in conjunction with the accompanying drawings, in which.

Corresponding reference characters indicate corresponding parts throughout the drawings.

DETAILED DESCRIPTION OF THE PREFERRED EMBODIMENTS

Figure 1A:
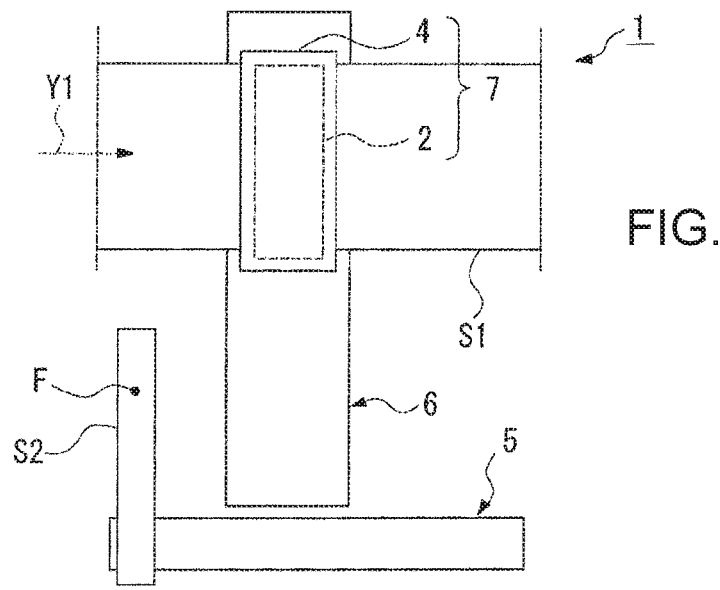
FIG. 1A is a schematic plan view showing a state at the time of sample inspection and FIG. 1B is a schematic plan view showing a state at the time of standard sample inspection in a first embodiment of a X-ray transmission inspection apparatus according to the present invention.
Figure 1B:
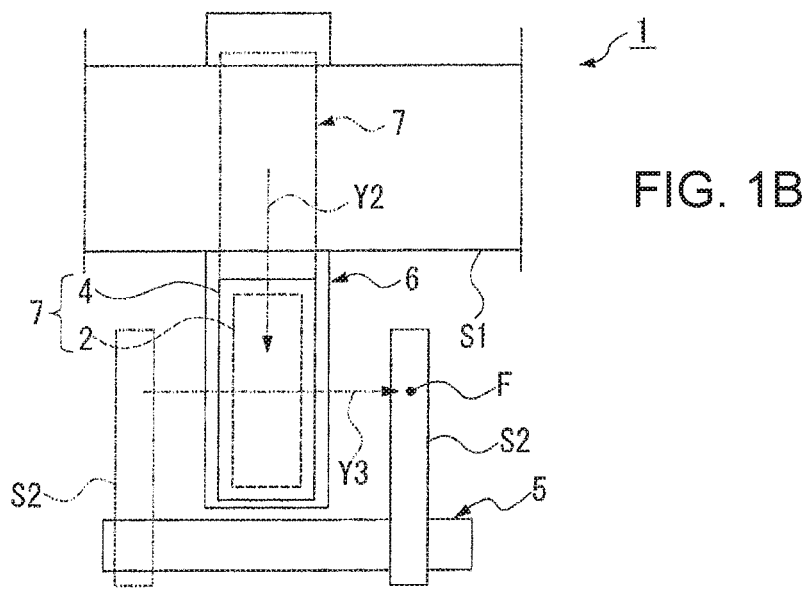
Figure 2:
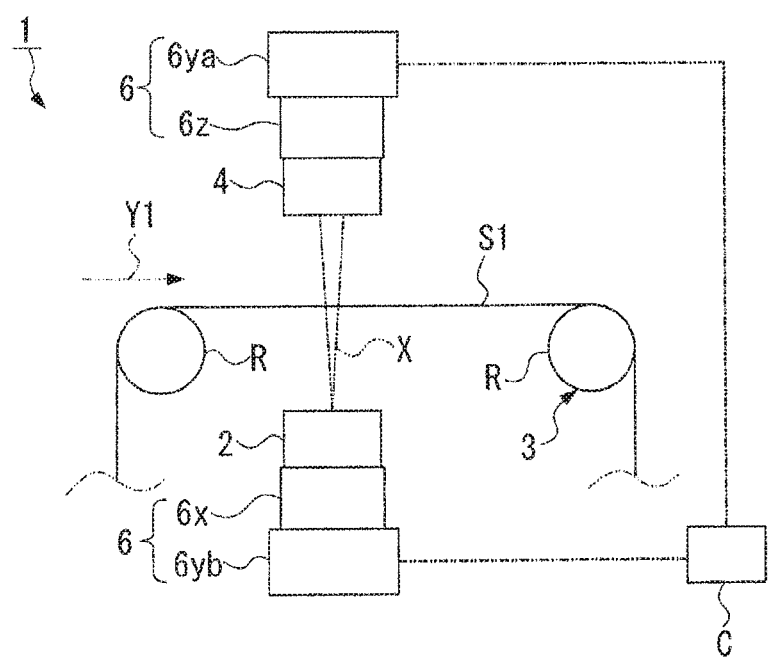
FIG. 2 is a schematic front view at the time of sample inspection showing the X-ray transmission inspection apparatus in the first embodiment.

Hereinafter, a first embodiment of an X-ray transmission inspection apparatus according to the present invention will be described with reference to FIGS. 1A, 1B, 2 and 3.

As shown in FIGS. 1A, 1B, 2 and 3, the X-ray transmission inspection apparatus 1 of the present embodiment includes an X-ray source 2 that irradiates X-rays X to a sample S1; a sample moving mechanism 3 that moves the sample S1 continuously in a predetermined direction while X-rays X are irradiated from the X-ray source 2; an X-ray detector 4 that is provided opposed to the X-ray source 2 with respect to the sample S1 and detects the X-rays X transmitted through the sample S1; a standard sample moving mechanism 5 configured to move a standard sample S2 placed in a different position from that of the sample S1; and an arrangement changing mechanism 6 configured to be in a such a manner that the X-ray source 2 and the X-ray detector 4, and the sample S1 and the standard sample S2 are movable relative to each other, and configured to change an arrangement state from one arrangement state in which the X-ray source 2 and the X-ray detector 4 face the sample S1 to the other arrangement state in which the X-ray source 2 and the X-ray detector 4 face the standard sample S2 that is moved by the standard sample moving mechanism 5.

It should be noted that the arrangement changing mechanism 6 of the present embodiment can move the X-ray source 2 and the X-ray detector 4 from a position in which the X-ray source 2 and the X-ray detector 4 face the sample S1 to a position in which the X-ray source 2 and the X-ray detector 4 face the standard sample S2 which is moved by the standard sample moving mechanism 5.

The X-ray source 2 and the X-ray detector 4 opposed to each other constitute an inspection unit 7.

Further, the X-ray transmission inspection apparatus 1 of the present embodiment includes a control unit C connected to the X-ray source 2 and the X-ray detector 4 to control the X-ray source 2 and the X-ray detector 4.

The control unit C is configured to perform the adjustment of the X-ray source 2 and the X-ray detector 4 when inspecting the sample S1 based on the result of inspecting the standard sample S2.

The control unit C is also connected to the sample moving mechanism 3, the standard sample moving mechanism 5, and the arrangement changing mechanism 6, and controls these mechanisms.

The control unit C is a computer composed of a CPU or the like. The control unit C includes an arithmetic processing circuit and the like. The arithmetic processing circuit performs an image processing based on a signal input from the X-ray detector 4 to create a transmission image and further displays the image on a display unit (not shown) such as a display.

The X-ray source 2 is an X-ray tube capable of emitting X-rays X, which are generated when thermoelectrons generated from a filament (cathode) in the tube are accelerated by a voltage applied between the filament (cathode) and a target (anode) to collide with W (tungsten), Mo (molybdenum), Cr (chrome), or the like of the target, as a primary X-rays from a window of beryllium foil or the like.

In the present embodiment, the X-ray source 2 is arranged to face the sample S1 below the sample S1 that moves between a pair of rollers R.

The sample S1 is, for example, a belt-shaped sample and is used for lithium-ion battery or medical use.

For example, in the case where the sample S1 is an electrode sheet or the like used in a lithium-ion ion secondary battery, the foreign matters F mixed therein is Fe, Pt, SUS, or the like, which may cause contamination of the electrode as foreign matters F.

The sample moving mechanism 3 has a configuration of a motor or the like for moving the sample S1 between the X-ray source 2 and the X-ray detector 4 arranged to face each other. For example, the sample moving mechanism 3 includes at least a pair of rollers R for moving the belt-shaped sample S1 in a roll-to-roll manner in the extending direction of the sample S1, a motor (not shown) for driving these, and the like.

In the present embodiment, a moving direction of the sample S1 between the pair of rollers R is defined as an X-axis direction, a direction which is orthogonal to the X-axis direction and is in horizontal direction is defined as a Y-axis direction, and a direction which is orthogonal to X- and Y-axis directions is defined as a Z-axis direction.

Figure 3:
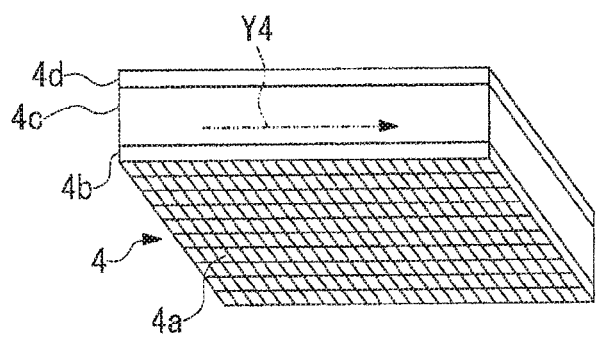
FIG. 3 is a perspective view showing an X-ray detector (TDI sensor) in the first embodiment.

As shown in FIG. 3, the X-ray detector 4 is a TDI (Time Delay Integration) sensor in which a plurality of cells (sensor elements) are arranged in each of a direction perpendicular to the moving direction of the sample S1 and a direction parallel thereto. The TDI sensor includes a phosphor 4b disposed on a detection surface 4a, an FOP (fiber optics plate) 4c in which a plurality of optical fibers are arranged in two dimensions vertically and horizontally beneath the phosphor 4b and a Si light receiving element 4d arranged under the FOP 4c. The TDI sensor has a structure in which line sensors are arranged to have a plurality of rows. For example, unit line sensors at 200 to 1000 stages are arranged in a feeding direction of the sample S1 so as to constitute the TDI sensor.

In this X-ray detector 4, a phosphor 4b such as CsI (cesium iodide), GOS (gadolinium oxysulfide) or YAG (yttrium aluminum garnet) is used.

In the present embodiment, the X-ray detector 4 is arranged above the moving sample S1 to face the sample S1.

Further, in the present embodiment, the TDI sensor is employed as the X-ray detector 4, but a CCD sensor such as a general line sensor or the like can be adopted.

The standard sample S2 is disposed adjacent to the sample S1 stretched between the pair of rollers R. Further, the standard sample S2 has a foreign matter F whose reference data such as size, element, material and position are known in advance. It is to be noted that the reference data of the foreign matter F is stored in advance in the control unit C.

The standard sample moving mechanism 5 is an X axis stage capable of moving the standard sample S2 along the moving direction (X axis direction) of the sample S1.

It should be noted that the standard sample moving mechanism 5 is capable of moving the standard sample S2 disposed near the sample S1 in parallel at the same height position as the sample S1.

The arrangement changing mechanism 6 includes a ray-source Y-axis stage 6yb that is capable of moving the X-ray source 2 in a direction orthogonal to the moving direction (X-axis direction) of the sample S1 and in a horizontal direction (hereinafter referred to as Y-axis direction), a ray-source Z-axis stage 6x that is capable of moving the X-ray source 2 in the Z-axis direction, a detector Y-axis stage 6ya that is capable of moving the X-ray detector 4 in the Y-axis direction, and a detector Z-axis stage 6z that is capable of moving the X-ray detector 4 in the Z-axis direction.

The arrow Y1 in the figure is the moving direction of the sample S1, the arrow Y2 is a moving direction of the inspection unit 7, and the arrow Y3 is a moving direction of the standard sample S2. Further, the arrow Y4 is a TDI driving direction of the X-ray detector 4 which is the TDI sensor.

Next, an adjustment method such as calibration of the inspection unit 7 using the X-ray transmission inspection apparatus 1 of the present embodiment will be described.

First, when inspecting the sample S1, the sample moving mechanism 3 moves the sample S1 between the X-ray source 2 and the X-ray detector 4 opposed to each other at a constant speed, and when performing the calibration, the irradiation of the X-rays X from the X-ray source 2 and the movement of the sample S1 are stopped.

Next, the arrangement changing mechanism 6 moves the inspection unit 7 to a position where the standard sample S2 can be inspected. That is, the X-ray source 2 is moved by the ray-source Y-axis stage 6yb to a position below the moving region of the standard sample S2 and at the same time the X-ray detector 4 is moved by the detector Y-axis stage 6ya to a position above the moving region of the standard sample S2 and facing the X-ray source 2.

Next, as described above, in the condition that the X-ray source 2 and the X-ray detector 4 have been retracted from the inspection position of the sample S1 and moved to the inspection position of the standard sample S2, the standard sample moving mechanism 5 moves the standard sample S2 in the direction Y3 along the moving direction Y1 of the sample S1 and at the same speed as that of the sample S1.

At this time, in the same manner as the inspection of the sample S1, the inspection unit 7 inspects the standard sample S2 and detects the foreign matter F in the standard sample S2. Further, based on the detected information and the reference data of the foreign matter F stored in advance, the control unit C adjusts the calibration etc. of the inspection unit 7.

As such, since the X-ray transmission inspection apparatus 1 of the present embodiment comprises the arrangement changing mechanism 6 configured to be capable of moving the X-ray source 2 and the X-ray detector 4 from the position facing the sample S1 to the position facing the standard sample S2 that is moved by the standard sample moving mechanism 5, when performing the adjustment such as calibration by the standard sample S2, the inspection of the standard sample S2 can be performed by retracting the X-ray source 2 and the X-ray detector 4 from the line which is the inspection position of the sample S1 by the arrangement changing mechanism 6, and accordingly, there is no interference with the sample S1, and maintenance of the inspection unit 7, etc. becomes easy. Therefore, since it is unnecessary to replace the sample S1 with the standard sample S2, it is not necessary to remove the sample S1 even during the inspection of a plurality of samples or a long sample S1, and adjustment such as calibration or the like can be easily performed.

Further, since the standard sample moving mechanism 5 can move the standard sample S2 arranged on the side of the sample S1 at the same speed as the sample S1 in the direction parallel to the moving direction of the sample S1, it is possible to easily inspect the standard sample S2 under the same conditions as the sample S1 by merely moving the X-ray source 2 and the X-ray detector 4 by the arrangement changing mechanism 6 to the positions facing the standard sample S2 on the side of the belt-shaped sample S1.

Further, since the control unit C adjusts the X-ray source 2 and the X-ray detector 4 when inspecting the sample S1 based on the result of inspecting the standard sample S2, the control unit C automatically performs the adjustment of calibration or the like of the X-ray source 2 and the X-ray detector 4 and therefore, stable and highly accurate measurement can be maintained.

Next, second to fourth embodiments of the X-ray transmission inspection apparatus according to the present invention will be described below with reference to FIGS. 4 to 9. In the following description of each embodiment, the same reference numerals are given to the same constituent elements described in the above embodiment, and description thereof will be omitted.

Figure 4:
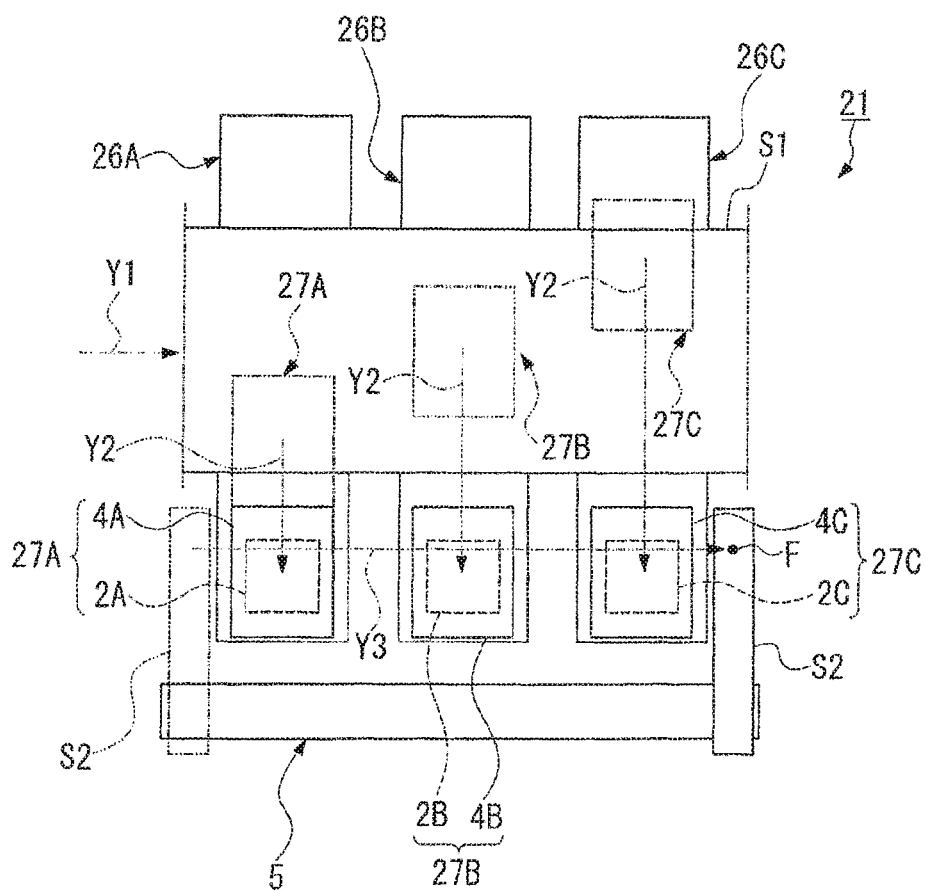
FIG. 4 is a schematic plan view showing a state at the time of standard sample inspection in a second embodiment of a X-ray transmission inspection apparatus according to the present invention.
Figure 5:
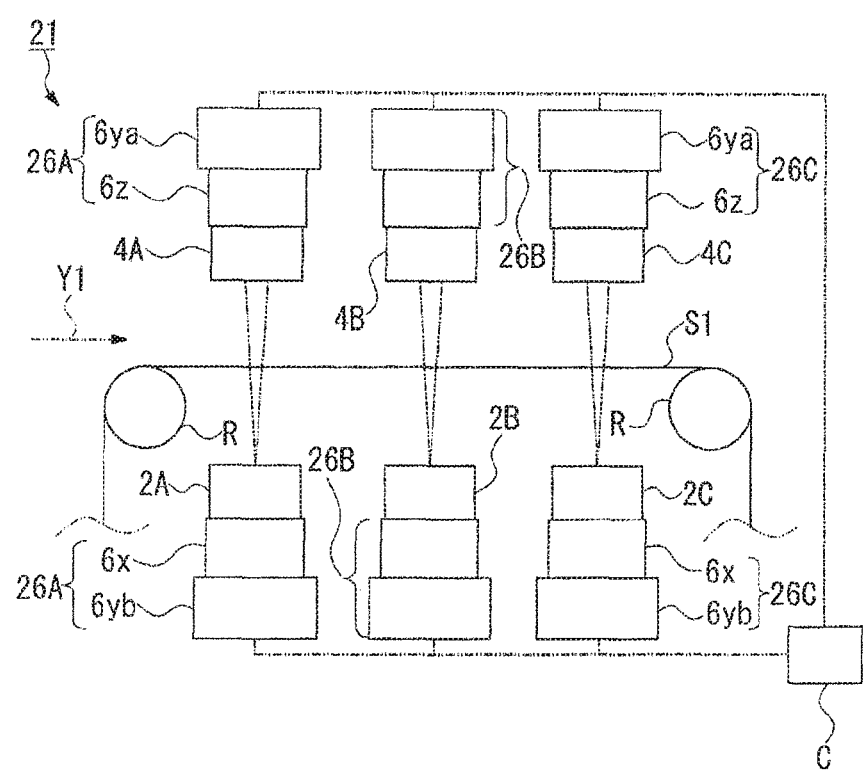
FIG. 5 is a schematic front view at the time of sample inspection showing the X-ray transmission inspection apparatus in the second embodiment.

The difference between the second embodiment and the first embodiment is that in the first embodiment, only one inspection unit 7 is provided, whereas in a X-ray transmission inspection apparatus 21 of the second embodiment, as shown in FIG. 4 and FIG. 5, a plurality of inspection units each including the X-ray source and the X-ray detector opposed to each other are provided, and the arrangement changing mechanism 6 is capable of moving the plurality of inspection units 27A, 27B, and 27C.

That is, the X-ray transmission inspection apparatus 21 of the second embodiment includes three inspection units 27A, 27B, and 27C and three arrangement changing mechanisms 26A, 26B, 26C corresponding to the inspection units 27A, 27B, and 27C.

The inspection unit 27A includes an X-ray source 2A and an X-ray detector 4A. The inspection unit 27B includes an X-ray source 2B and an X-ray detector 4B. The inspection unit 27C includes an X-ray source 2C and an X-ray detector 4C.

The inspection units 27A, 27B, and 27C are provided with small X-ray sources 2A, 2B, and 2C and X-ray detectors 4A, 4B, and 4C having narrower inspection regions than the width of the sample S1.

When inspecting the sample S1, the inspection unit 27A is arranged on the upstream side of the inspection line of the sample S1, and the inspection unit 27B is arranged on the downstream side than the inspection unit 27A. Further, the inspection unit 27C is arranged on the downstream side than the inspection unit 27B.

Further, when inspecting the sample S1, the inspection units 27A, 27B, and 27C are arranged at positions different from each other in the width direction of the sample S1. That is, the inspection unit 27A is arranged to face a position biased toward the standard sample S2 in the width direction of the sample S1, the inspection unit 27B is arranged to face a center position in the width direction of the sample S1, and the inspection unit 27C are arranged to face a position biased toward the side opposite to the standard sample S2 side in the width direction of the sample S1. Thereby, it is possible to inspect the entire width direction of the sample S1 by performing inspections divided by the three inspection units 27A, 27B, and 27C. Therefore, smaller X-ray source and X-ray detector than the inspection unit 7 of the first embodiment can be adopted as each of the inspection units 27A, 27B, and 27C, and even if the sample S1 is a wide sample, it is also possible to inspect the entire width of the sample S1 in the width direction.

In the second embodiment, when calibrating each of the inspection units 27A, 27B, and 27C, etc., as shown in FIG. 4, it is possible to move each of the inspection units 27A, 27B, 27C individually or entirely by the arrangement changing mechanisms 26A, 26B and 26C to the moving region of the standard sample S2 and inspect the standard sample S2.

As described above, in the X-ray transmission inspection apparatus 21 of the second embodiment, since the arrangement changing mechanisms 26A, 26B, and 26C can move the plurality of inspection units 27A, 27B, and 27C, the plurality of inspection units 27A, 27B, and 27C can be adjusted simultaneously or individually with the standard sample S2.

In particular, since the arrangement changing mechanisms 26A, 26B, and 26C are capable of moving the plurality of inspection units 27A, 27B, and 27C to different positions in the width direction of the sample S1 when inspecting the sample S1, it is possible to divide the width direction of the sample S1 into a plurality of positions and inspect the different positions in the width direction of the sample S1 separately with the inspection units 27A, 27B, and 27C.

Therefore, even if the inspection unit is not a large-sized inspection unit, it is possible to perform inspection in a wide range in the width direction of the sample S1 with a plurality of small inspection units 27A, 27B, and 27C, and it is possible to irradiate the X-rays X on only a specific position in the width direction and perform inspection of the sample S1. Further, by moving the plurality of inspection units 27A, 27B, and 27C to positions to face the standard sample S2, it is possible to inspect the plurality of inspection units 27A, 27B, and 27C simultaneously or individually with the standard sample S2.

Figure 6:
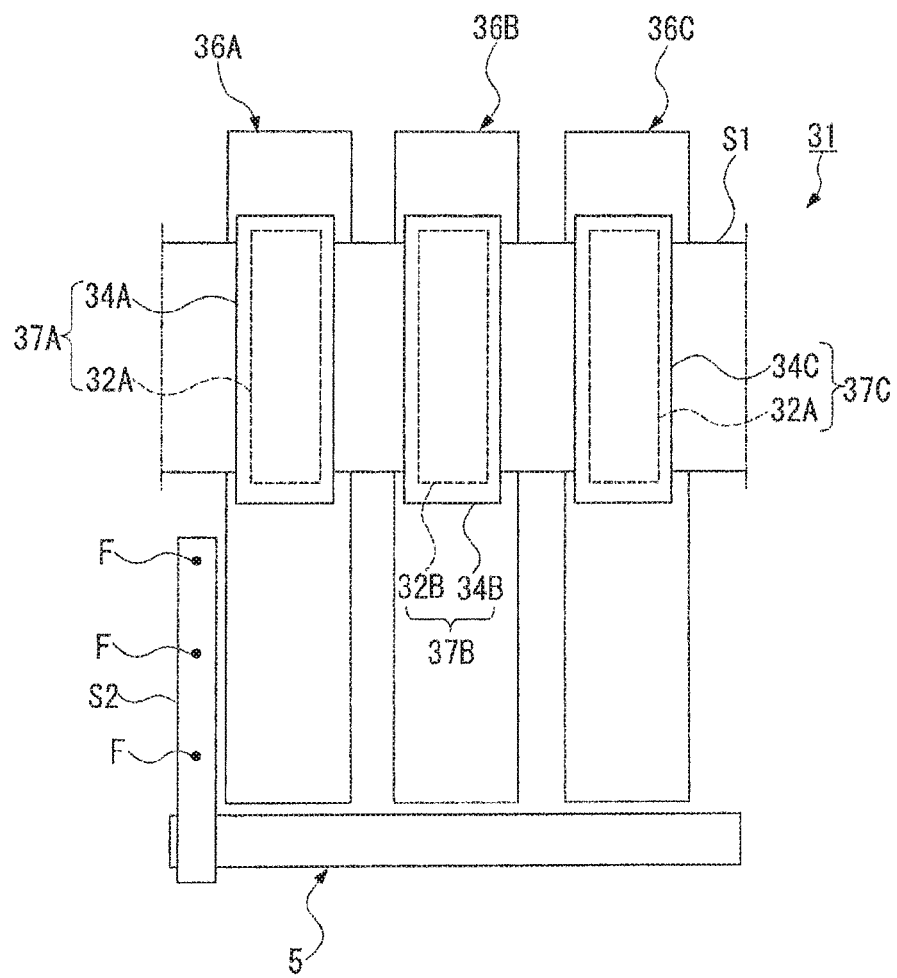
FIG. 6 is a schematic plan view showing a state at the time of sample inspection in a third embodiment of a X-ray transmission inspection apparatus according to the present invention.
Figure 7:
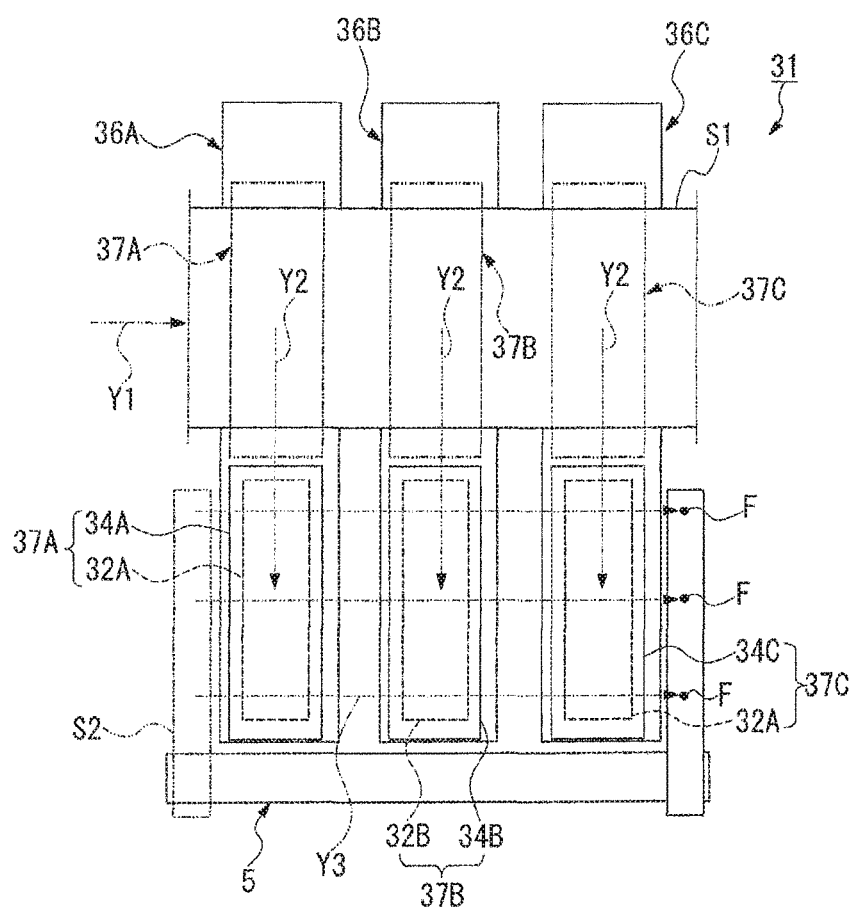
FIG. 7 is a schematic plan view showing a state at the time of standard sample inspection in the third embodiment.

Next, the difference between the third embodiment and the second embodiment is that, in the second embodiment, the three small inspection units 27A, 27B, and 27C are arranged at different positions in the width direction of the sample S1 while, in the X-ray transmission inspection apparatus 31 of the third embodiment, as shown in FIGS. 6 and 7, large inspection units 37A, 37B, and 37C capable of inspecting the entire width of the sample S1 are arranged side by side in the moving direction of the sample S1.

In other words, in the third embodiment, each of the inspection units 37A, 37B, and 37C has an inspection area that is the same as or wider than the width of the sample S1, and is arranged at the same position in the width direction of the sample S1.

Therefore, each of the inspection units 37A, 37B, and 37C employs a corresponding one of X-ray sources 32A, 32B, and 32C and a corresponding one of X-ray detectors 34A, 34B, and 34C which are larger than those of the inspection units 27A, 27B, and 27C according to the second embodiment, and, accordingly, it is possible for each of them to individually inspect the entire width direction of the sample S1.

Also in the third embodiment, when calibrating each of the inspection units 37A, 37B, and 37C, etc., as shown in FIG. 7, it is possible to move each of the inspection units 37A, 37B, and 37C individually or entirely by the arrangement changing mechanisms 36A, 36B, and 36C to the moving region of the standard sample S2 and inspect the standard sample S2.

Incidentally, the X-ray detectors 34A, 34B, and 34C according to the present embodiment need not be TDI sensors, and CCD sensors such as general line sensors can also be adopted. In this case, by integrating the detection signals of the X-ray detectors 34A, 34B, and 34C of the CCD sensors arrayed in multiple stages, it is also possible to make TDI. In addition, by increasing the number of the inspection units by N times, the moving speed of the sample S1 can also be increased by N times, and the throughput can also be improved. In this way, the above configuration even can cope with the task of improving the throughput.

Furthermore, for the respective inspection units 37A, 37B, and 37C of the respective X-ray sources 32A, 32B, and 32C and the respective X-ray detector 34A, 34B, and 34C, it is possible to individually adjust the ray type of the respective X-ray source. That is, when the foreign matters F such as different elements or materials are detected by individually changing the ray type of the X-ray sources 32A, 32B, and 32C and imaging with the corresponding X-ray detectors 34A, 34B, and 34C, it is also possible to detect these foreign matters simultaneously by a single measurement without changing the type of X-ray for each of corresponding foreign matters F to perform a plurality of measurements.

For example, by using two pairs of X-ray sources and X-ray detectors out of each of the X-ray sources 32A, 32B, and 32C and the X-ray detectors 34A, 34B, and 34C and separately specifying the ray type to be suitable to detect Fe and Pt, respectively, these foreign matters F can be simultaneously detected just by having the sample S1 flow once. Conventionally, it has been necessary to have the sample S1 flow a plurality of times when inspecting foreign matters F having different elements, materials, or the like. However, by the inspection units 37A and 37B of the respective stages having different types of X-ray, it is possible to detect various foreign matters F by a single measurement.

Further, identification of a certain representative element included in the objects to be measured can be achieved as an image of a foreign matter containing an element of interest, by subtraction of an image of each of foreign matters obtained by adapting the type of X-ray for each of different foreign matters F.

Thus, in the X-ray transmission inspection apparatus 31 of the third embodiment, when inspecting the sample S1, since the arrangement changing mechanism 36A, 36B, and 36C are capable of moving a plurality of the inspection units 37A, 37B, and 37C, to the same position in the width direction of the sample S1, it becomes possible to inspect the same position of the sample S1 in multiple stages by a plurality of the inspection units 37A, 37B, and 37C. Accordingly, foreign matters F become detectable with higher accuracy. Further, for example, in response to a plurality of different foreign matters F such as Fe, Pt and the like, by changing the ray type of each of the X-ray source 32A, 32B, and 32C to a predetermined ray type, different foreign matters F can be detected by a single measurement. Further, by inspecting the same position at a plurality of the inspection units 37A, 37B, and 37C, it also becomes possible to increase the scanning speed of the sample S1.

Figure 8:
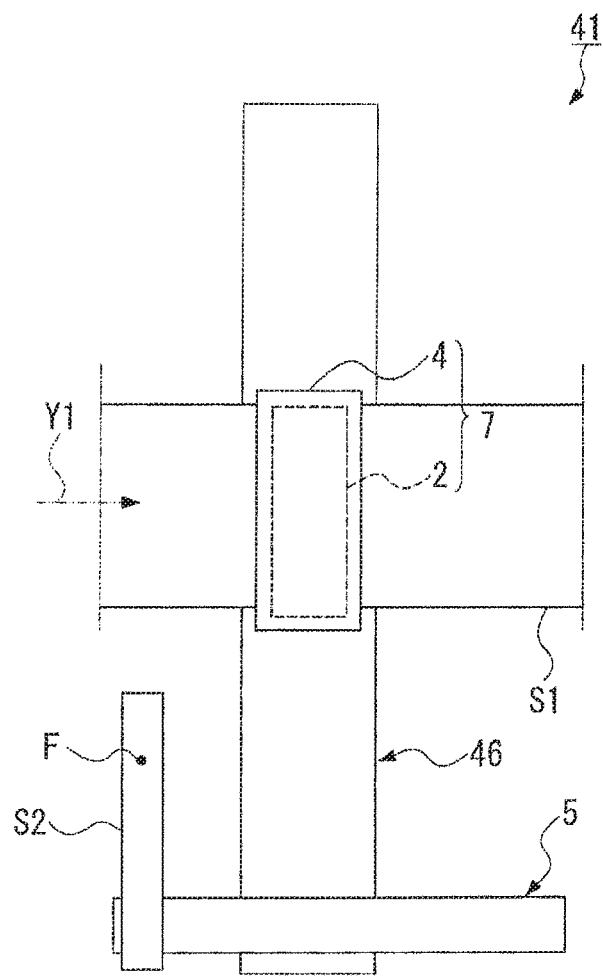
FIG. 8 is a schematic plan view showing a state at the time of sample inspection in a fourth embodiment of a X-ray transmission inspection apparatus according to the present invention.
Figure 9:
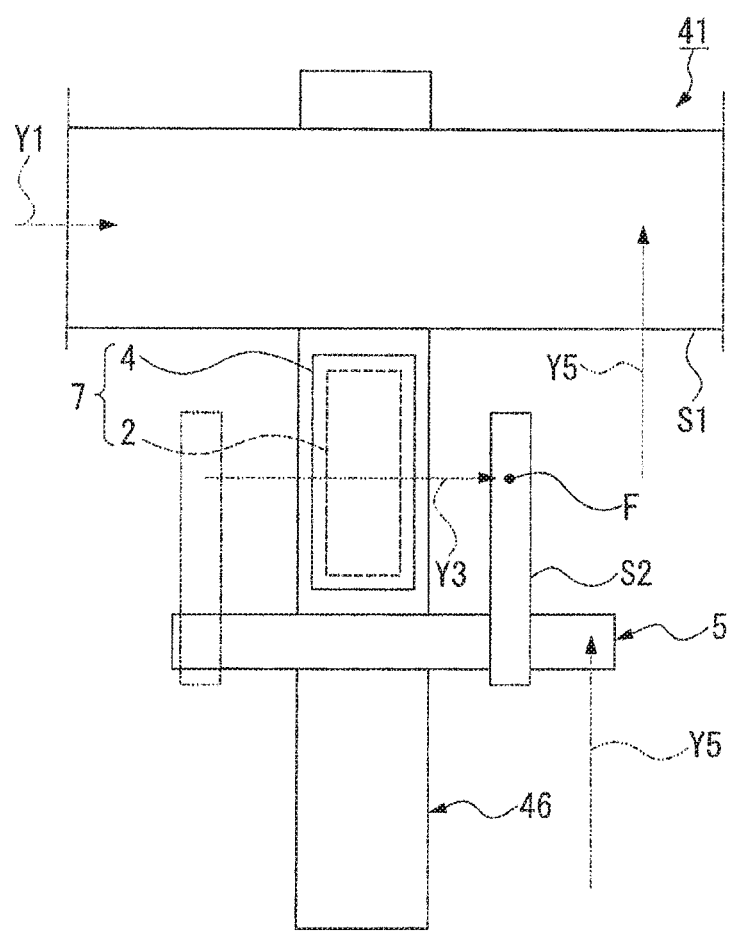
FIG. 9 is a schematic plan view showing a state at the time of standard sample inspection in the fourth embodiment.

Next, the difference between a fourth embodiment and the first embodiment is that, in the first embodiment, the arrangement changing mechanism 6 moves the X-ray source 2 and the X-ray detector 4 from the position facing the sample S1 to the position to face the standard sample S2 that is moved by the standard sample moving mechanism 5 while, in the X-ray transmission inspection apparatus 41 of the fourth embodiment, as shown in FIGS. 8 and 9, the arrangement changing mechanism 46 is capable of retracting the samples S1 from the position facing the X-ray source 2 and the X-ray detector 4 and at the same time moving the standard sample S2 to the position to face the X-ray source 2 and the X-ray detector 4.

That is, in the fourth embodiment, the arrangement changing mechanism 46 is provided with a Y-axis stage configured to be capable of laterally sliding the sample S1, the pair of rollers R, the standard sample moving mechanism 5 and the standard sample S2 simultaneously to the Y-axis direction.

Further, arrows Y5 in FIG. 9 is a sliding direction of the sample S1 and the standard sample S2.

In this manner, in the fourth embodiment, the arrangement changing mechanism 46 is configured to move the samples S1 and the standard sample S2, not the X-ray source 2 and the X-ray detector 4, thereby changing an arrangement state from one arrangement state in which the X-ray source 2 and the X-ray detector 4 face the sample S1 to the other arrangement state in which the X-ray source 2 and the X-ray detector 4 face the standard sample S2 that is moved by the standard sample moving mechanism 5.

Therefore, like the first embodiment, in the fourth embodiment, the X-ray source 2 and the X-ray detector 4, and the sample S1 and the standard sample S2 are relatively movable. Accordingly, when performing adjustment of calibration, etc. by standard sample S2, the inspection of the standard sample S2 can be performed by retracting the sample S1 from the position facing the X-ray source 2 and the X-ray detector 4 and arranging the standard sample S2 to the position to face the X-ray source 2 and the X-ray detector 4 by the arrangement changing mechanism 46.

The technical scope of the present invention is not limited to the above embodiments and can be modified variously without departing from the scope of the present invention.

For example, although the second and third embodiments adopt three inspection units, two or four or more inspection units may be employed.

In the above embodiments, either the movement of the sample and standard sample or the movement of the X-ray source and X-ray detector is performed by the arrangement changing mechanism, but an arrangement changing mechanism capable of performing the both movements may be adopted.

When introducing elements of aspects of the disclosure or the embodiments thereof, the articles "a", "an", "the" and "said" are intended to mean that there are one or more of the elements. The terms "comprising", "including", and "having" are intended to be inclusive and mean that there may be additional elements other than the listed elements.

Having described aspects of the disclosure in detail, it will be apparent that modifications and variations are possible without departing from the scope of aspects of the disclosure as defined in the appended claims. As various changes could be made in the above constructions, products, and methods without departing from the scope of aspects of the disclosure, it is intended that all matter contained in the above description and shown in the accompanying drawings shall be interpreted as illustrative and not in a limiting sense.

What is claimed is:

1. An X-ray transmission inspection apparatus, comprising:
    an X-ray source that irradiates X-rays to a sample;
    a sample moving mechanism that moves the sample continuously in a predetermined direction while X-rays are irradiated from the X-ray source;
    an X-ray detector that is provided opposed to the X-ray source with respect to the sample and detects the X-rays transmitted through the sample;
    a standard sample moving mechanism configured to move a standard sample placed in a different position from that of the sample; and
    an arrangement changing mechanism configured to be in a such a manner that the X-ray source and the X-ray detector, and the sample and the standard sample are movable relative to each other, and configured to change an arrangement state from one arrangement state in which the X-ray source and the X-ray detector face the sample to the other arrangement state in which the X-ray source and the X-ray detector face the standard sample that is moved by the standard sample moving mechanism.

2. The X-ray transmission inspection apparatus according to claim 1, wherein a plurality of inspection units each comprising the X-ray source and the X-ray detector opposed to each other are provided, and wherein the arrangement changing mechanism is configured to move the plurality of inspection units.

3. The X-ray transmission inspection apparatus according to claim 1, wherein the sample is a belt-shaped sample, and the sample moving mechanism moves the sample in its extending direction, and wherein the standard sample moving mechanism is configured to move the standard sample arranged on the side of the sample at the same speed as the sample in a direction parallel to the moving direction of the sample.

4. The X-ray transmission inspection apparatus according to claim 1, further comprising a control unit which is connected to the X-ray source and the X-ray detector to control the X-ray source and the X-ray detector,
    wherein the control unit is configured to perform an adjustment of the X-ray source and the X-ray detector when inspecting the sample based on the result of inspecting the standard sample.

5. The X-ray transmission inspection apparatus according to claim 2, wherein the arrangement changing mechanism is configured to move the plurality of the inspection units to different positions in the width direction of the sample when inspecting the sample.

6. The X-ray transmission inspection apparatus according to claim 2, wherein the arrangement changing mechanism is configured to move the plurality of the inspection units in the same position in the width direction of the sample when inspecting the sample.

* * * * *